United States Patent
Takai et al.

(10) Patent No.: US 8,299,313 B2
(45) Date of Patent: Oct. 30, 2012

(54) OLEFIN PRODUCTION PROCESS

(75) Inventors: Toshihiro Takai, Nishinomiya (JP); Hirokazu Ikenaga, Ichihara (JP); Makoto Kotani, Yokohama (JP); Satoru Miyazoe, Kamakura (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/060,578

(22) PCT Filed: Aug. 27, 2009

(86) PCT No.: PCT/JP2009/064934
§ 371 (c)(1), (2), (4) Date: Feb. 24, 2011

(87) PCT Pub. No.: WO2010/024319
PCT Pub. Date: Mar. 4, 2010

(65) Prior Publication Data
US 2011/0152595 A1 Jun. 23, 2011

(30) Foreign Application Priority Data
Aug. 28, 2008 (JP) .................. 2008-219626

(51) Int. Cl.
*C07C 2/88* (2006.01)
(52) U.S. Cl. ........ 585/637; 585/664; 585/665; 585/666; 585/670
(58) Field of Classification Search .................. 585/637, 585/664–666, 670
See application file for complete search history.

(56) References Cited

U.S. PATENT DOCUMENTS

| | | | |
|---|---|---|---|
| 3,658,929 A | 4/1972 | Banks | |
| 4,575,575 A | 3/1986 | Drake et al. | |
| 2004/0106835 A1 | 6/2004 | Gartside et al. | |
| 2005/0014981 A1 | 1/2005 | Gartside et al. | |
| 2005/0124839 A1 | 6/2005 | Gartside et al. | |
| 2006/0161033 A1 | 7/2006 | Chodorge et al. | |
| 2007/0142258 A1 | 6/2007 | Steinbrenner et al. | |
| 2008/0146856 A1 | 6/2008 | Leyshon | |
| 2008/0188696 A1 | 8/2008 | Stephan et al. | |
| 2008/0194903 A1 | 8/2008 | Schubert et al. | |
| 2008/0312485 A1 | 12/2008 | Takai et al. | |
| 2010/0063339 A1 | 3/2010 | Takai et al. | |
| 2011/0160504 A1 | 6/2011 | Stephan et al. | |

FOREIGN PATENT DOCUMENTS

| | | |
|---|---|---|
| EP | 1854776 | 2/2006 |
| JP | 46-1664 | 9/1971 |
| WO | 2006/052688 A2 | 5/2006 |
| WO | 2006/093058 | 9/2006 |
| WO | 2007/055361 | 5/2007 |
| WO | 2008/136280 | 11/2008 |
| WO | 2009/013964 | 1/2009 |

OTHER PUBLICATIONS

Borg, O. et al. (2007). Topics in Catalysis, 45, 1-4, 39-43.*
International Search Report dated Dec. 1, 2009.
Applied Industrial Catalysis, vol. 3, pp. 215-239, 1984.
Search Report and Written Opinion prepared by Hungarian Patent Office issued in connection with the corresponding Singapore application (201101398-4) dated Jun. 26, 2012.

* cited by examiner

*Primary Examiner* — Walter D Griffin
*Assistant Examiner* — Brian McCaig
(74) *Attorney, Agent, or Firm* — Rankin, Hill & Clark LLP

(57) ABSTRACT

A process is provided which is capable of producing olefins stably and efficiently by a metathesis reaction of identical or different olefins while preventing the lowering in metathesis catalyst activity due to trace impurities such as heteroatom-containing compounds that are contained in a starting olefin. The olefin production process includes supplying a starting olefin containing more than 0 ppm by weight to not more than 10 ppm by weight of one or more kinds of heteroatom-containing compounds to a reactor that contains a metathesis catalyst and an isomerization catalyst, the metathesis catalyst including at least one metal element selected from the group consisting of tungsten, molybdenum and rhenium, the isomerization catalyst including calcined hydrotalcite or yttrium oxide, and performing a metathesis reaction of identical or different olefins.

13 Claims, No Drawings

OLEFIN PRODUCTION PROCESS

TECHNICAL FIELD

The present invention relates to processes for producing olefins by a metathesis reaction of identical or different olefins.

BACKGROUND ART

A metathesis reaction involves identical or different olefins that are reacted with each other and affords olefins having a different structure. This reaction is very advantageous because it can cope with changes in olefin demands by inter-converting ethylene, propylene, butenes and the like that are produced by naphtha cracking at certain proportions.

Olefin production processes by a metathesis reaction have been improved. For example, Patent Document 1 discloses a process of producing propylene by a metathesis reaction of ethylene and 2-butene wherein the conversion is increased by using a catalyst mixture that contains a silica-supported tungsten oxide catalyst $WO_3/SiO_2$ and a magnesium oxide catalyst. Patent Document 2 discloses a process of producing propylene by a metathesis reaction of ethylene and n-butene which involves a metathesis catalyst/co-catalyst mixture and a small amount of hydrogen whereby the metathesis reaction can take place at a sufficiently high industrial reaction rate even at low temperatures.

However, the catalysts used in the metathesis reaction (hereinafter, also the metathesis catalysts) lower activity with time, though the deterioration degrees vary depending on reaction conditions, starting olefins or catalyst types. In particular, the catalytic activity is quickly lowered due to catalyst poisoning by impurities contained in starting olefins. For example, Non-Patent Document 1 describes that the catalytic activity is deteriorated over time due to catalyst poisoning by trace impurities contained in starting olefins (such as oxygen-containing compounds such as water, alcohols, ketones and ethers, and sulfur-containing compounds such as mercaptans and thiophenes) or due to coking that is deposition of heavy by-products on the catalysts.

These problems are addressed by sufficiently removing impurities from starting olefins beforehand by for example distillation, hydrogenation, extraction or adsorption. Alternatively, the catalysts are regenerated at regular intervals by passing an oxygen-containing gas through the reactor at high temperature to burn off poisonous substances or heavy deposits attached on the catalysts, thereby maintaining catalytic activity.

In particular, the metathesis catalysts are very liable to be poisoned by impurities, and quickly reduce the activity in the presence of very trace amounts of impurities. Therefore, it is necessary that starting olefins are purified thoroughly to remove impurities contained in the starting olefins. In general, adsorption is an effective purification method for removing trace amounts of impurities. In detail, an unpurified starting olefin is passed through an adsorption purification column filled with an inorganic material (an adsorbent) capable of high adsorption performance. Patent Document 3 describes that trace unidentified impurities contained in a starting olefin are removed with use of magnesium oxide, and the metathesis catalyst activity is greatly improved as a result.

Similar to the catalysts, the adsorbents also lower performance with time and thus they are regularly regenerated by burning off substances adsorbed thereto by passing an oxygen-containing gas at high temperature, or by detaching substances adsorbed thereto by passing an inert gas such as nitrogen.

However, insufficient regeneration or over-time degradation of adsorbents results in very trace amounts of impurities remaining in starting olefins. Such impurities are supplied to a metathesis reactor and poison the catalyst to drastically lower the metathesis catalytic activity. This problem could be coped with by exchanging the adsorbents more frequently or increasing the number of adsorption purification columns. These countermeasures, however, greatly increase costs.

Alternatively, a metathesis reaction step and a catalyst regeneration step may be operated at shorter cycles and the regeneration temperature may be raised to shorten the regeneration time whereby the reactions are repeatedly conducted for short periods but with high catalytic activity. However, catalysts and in particular isomerization catalysts such as magnesium oxide greatly reduce the surface area upon regeneration at high temperatures. The surface area of catalysts is a factor that determines catalytic performances, and a larger surface area provides a higher catalytic performance. Therefore, a reduced surface area of a catalyst by high temperature regeneration leads to lower catalytic activity. Thus, processes involving regeneration at high temperatures are not practical.

CITATION LIST

Patent Literature

Patent Document 1: U.S. Pat. No. 4,575,575
Patent Document 2: WO 2006/093058
Patent Document 3: U.S. Pat. No. 3,658,929

Non Patent Literature

Non-Patent Document 1: Applied Industrial Catalysis, Volume 3, p. 220

SUMMARY OF INVENTION

Technical Problem

It is an object of the invention to provide a process capable of producing olefins stably and efficiently by a metathesis reaction of identical or different olefins while preventing the lowering in metathesis catalyst activity due to trace impurities such as heteroatom-containing compounds that are contained in a starting olefin.

Solution to Problem

The present inventors studied diligently and have found that a metathesis catalyst and an isomerization catalyst including calcined hydrotalcite or yttrium oxide can catalyze a metathesis reaction of identical or different olefins while preventing the lowering in metathesis catalyst activity due to trace impurities such as heteroatom-containing compounds that are contained in a starting olefin, and can thereby afford olefins stably and efficiently over long periods. This advantageous effect is more marked when a starting olefin gas is fed at a superficial velocity of 0.01 to 2.0 m/sec.

Advantageous Effects of Invention

According to the olefin production processes of the present invention, the metathesis catalyst activity is maintained stably for long periods even if the starting olefin contains trace amounts of impurities such as heteroatom-containing compounds. Accordingly, no special equipment is required such as adsorption purification columns for purifying starting olefins, and olefins can be produced with significant advantages in the aspects of safety, processing and costs. Further, isomerization catalysts including calcined hydrotalcite or yttrium oxide possess high thermal stability, and therefore the catalysts may be regenerated at higher temperatures. As a result, the catalyst regeneration time may be shortened and a metathesis reaction step and a catalyst regeneration step may be operated at shorter cycles, enabling efficient olefin production.

DESCRIPTION OF EMBODIMENTS

An olefin production process according to the present invention comprises supplying a starting olefin containing more than 0 ppm by weight to not more than 10 ppm by weight of one or more kinds of heteroatom-containing compounds to a reactor that contains a metathesis catalyst and an isomerization catalyst including calcined hydrotalcite or yttrium oxide, and performing a metathesis reaction of identical or different olefins to produce an olefin having another different structure.

Starting olefins used in the olefin production generally contain one or more kinds of heteroatom-containing compounds as impurities in trace amounts as described above. Such impurities contained in the starting olefins lower the activity of metathesis catalysts and hinder long-term stable olefin production. Thus, conventional olefin production processes by a metathesis reaction involve removing impurities from starting olefins to make sure that identical or different olefins are reacted into other kinds of olefins stably over long periods while the metathesis catalysts maintain activity. The removal of impurities requires special equipment such as adsorption purification columns.

In the olefin production processes of the present invention, a metathesis reaction of identical or different olefins is catalyzed by a metathesis catalyst and an isomerization catalyst including calcined hydrotalcite or yttrium oxide. The metathesis catalyst is prevented from degradation and the metathesis reaction activity is maintained stably for long periods even if starting olefins contain trace amounts of impurities such as heteroatom-containing compounds. As a result, identical or different olefins are stably and efficiently reacted by a metathesis reaction to afford olefins having another different structure.

The metathesis catalysts in the invention contain at least one metal element selected from tungsten, molybdenum and rhenium. In particular, metathesis catalysts containing tungsten are preferable. The structures of tungsten, molybdenum and rhenium are not limited, and oxides, sulfides and hydroxides may be used. In particular, oxides such as $WO_3$, $MoO_3$ and $Re_2O_7$ are preferable, and $WO_3$ is more preferable. These oxides, sulfides or hydroxides may be supported on inorganic compounds called supports. The supports are not particularly limited, and examples thereof include silica, alumina and titania, with silica being particularly preferable. The supporting methods may be conventional and are not particularly limited. The amount of the metal element relative to the support may be, for example in the case of oxides, 0.01 wt % to 50 w %, and more preferably 0.1 wt % to 20 wt % in terms of oxide.

In the invention, calcined hydrotalcite is a $MgO.Al_2O_3$ solid solution obtained by calcining at 300° C. or above a hydrotalcite of Formula (i) below which is a layered magnesium-aluminum double hydroxide.

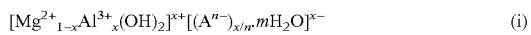

$$[Mg^{2+}{}_{1-x}Al^{3+}{}_x(OH)_2]^{x+}[(A^{n-})_{x/n}.mH_2O]^{x-} \quad (i)$$

wherein A is an anion, n is a valence of the anion A, x usually ranges from 0.20 to 0.33, and m is usually an integer of about 0 to 4 although greatly variable depending on the dehydration degree.

Examples of the anions A include carbonate ion, sulfate ion, hydroxide ion, fluoride ion, chloride ion, bromide ion and iodide ion.

The calcined hydrotalcite may be identified by for example powder X-ray diffraction (XRD). The calcined hydrotalcite shows a broad peak at the same diffraction angle as magnesium oxide. When the calcined hydrotalcite is soaked in water overnight and is thereafter dried at about 100° C., XRD provides a diffraction peak assigned to hydrotalcite.

The isomerization catalysts used in the invention contain the calcined hydrotalcite or yttrium oxide. The calcined hydrotalcite or yttrium oxide may be used singly as the isomerization catalyst, or they may be supported on inorganic compounds called supports. The calcined hydrotalcite or yttrium oxide may be obtained by known methods in the art without limitation. For example, yttrium hydroxide or hydrotalcite may be formed by a precipitation method or a coprecipitation method and may be decomposed at high temperatures. Alternatively, commercially available yttrium acetate, yttrium nitrate or yttrium carbonate may be decomposed at high temperatures. The supporting methods may be conventional in the art without limitation. The supports are not particularly limited, and examples thereof include silica, alumina and titania.

The shapes of the metathesis catalysts and the isomerization catalysts (hereinafter, these catalysts may be collectively referred to as the catalysts) are not particularly limited. The sizes of the catalysts may be selected appropriately depending on the size of reactors. The catalysts may be shaped by known methods in the art without limitation.

The metathesis catalyst and the isomerization catalyst may be physically mixed together or may be supported together on a single support. The catalyst may contain the metathesis catalyst and the isomerization catalyst at any proportions without limitation but tends to catalyze a metathesis reaction more effectively when the weight ratio of the isomerization catalyst is 50% or more relative to the total catalyst weight.

The metathesis reaction temperature is generally in the range of 25 to 500° C., preferably 100 to 400° C., and more preferably 200 to 350° C. This metathesis reaction temperature ensures that the catalysts adsorb reduced amounts of impurities such as heteroatom-containing compounds contained in starting olefins and are thereby prevented from degradation and tend to maintain metathesis reaction activity for long periods. This tendency is more prominent at higher reaction temperatures. The metathesis reaction pressure is generally in the range of 0.1 to 20 MPaG, and preferably 0.1 to 10 MPaG.

The amount of the catalysts is not particularly limited. For example, when the metathesis reaction is carried out using a fixed-bed flow apparatus, WHSV is preferably in the range of 1 to 500 $h^{-1}$, and more preferably 1 to 250 $h^{-1}$ wherein the WHSV represents the amount (weight) of starting olefin per unit time divided by the weight of the metathesis catalyst.

The metathesis reaction may be carried out in any mode without limitation, but a gas phase flow reaction is preferable. The catalyst packing modes include fixed beds, fluidized beds and suspended beds.

In a preferred embodiment, the catalysts are activated prior to the metathesis reaction by calcining the catalysts at high temperatures under a stream of an inert gas such as nitrogen thereby to detach and remove water, carbon dioxide and organic matters attached to the catalysts, and thereafter reducing the catalysts with reductive gases such as carbon monoxide and hydrogen. This pretreatment may be carried out by known methods in the art without limitation.

The olefin production processes of the invention may include a step in which the metathesis catalyst and the isomerization catalyst are regenerated at 500° C. or above after the metathesis reaction. The temperature in the catalyst regeneration is preferably in the range of 500 to 700° C., and more preferably 500 to 600° C. The regeneration temperature in this range permits quick catalyst regeneration and efficient olefin production as a result.

In an exemplary catalyst regeneration process, an oxygen-containing gas is passed through the reactor at a temperature of 500° C. or above to quickly burn off poisonous substances or heavy deposits attached on the catalysts during the reaction. The catalyst regeneration may be performed by known methods in the art without limiting the scope of the invention.

The starting olefins used in the invention are not particularly limited, bur lower olefins are preferable. Examples of the olefins include ethylene, propylene, 1-butene, 2-butene, 2-pentene, 2-hexene, 4-methyl-2-pentene and 3-methyl-1-butene. The olefins may be used singly, or two or more kinds may be used in combination. Starting olefins including ethylene and 2-butene give propylene. Starting olefins including ethylene and 2-pentene give propylene and 1-butene. Starting olefins including ethylene and 2-hexene give propylene and 1-pentene. Starting olefins including ethylene and 2-methyl-2-butene give propylene and isobutene. Starting olefins including ethylene and 4-methyl-2-pentene give propylene and 3-methyl-1-butene. Since the metathesis reactions are reversible, the above exemplary reactions may be reversed by selecting reaction conditions and the starting olefins may be produced from the olefins produced.

In the metathesis reaction, olefins are used as reaction materials. From the viewpoint of production efficiency, starting olefins are preferably free from saturated hydrocarbons such as methane, ethane, propane, n-butane, isobutane, pentane and hexane. However, the alkanes do not inhibit the metathesis reaction and thus may be present in the starting olefins.

When two or more kinds of olefins are used in the metathesis reaction, the amounts of the olefins in the starting olefins (the molar ratio) are not particularly limited. When the two or more kinds of olefins include ethylene, the ethylene content is preferably in excess over the other olefins contained in the starting olefins. For example, when ethylene and 2-butene are reacted to give propylene, the molar ratio of ethylene to n-butene (the total of 1-butene and 2-butene) (ethylene/n-butene) is generally in the range of 1 to 50, and preferably about 1 to 5. If this ratio is too small, reaction preferentially takes place between butenes. If the ratio is too large, considerable equipment and energy are required to recover unreacted ethylene.

In a particularly preferred embodiment of the olefin production processes, the starting olefins include ethylene and n-butene, the metathesis reactions include a metathesis reaction between ethylene and 2-butene, and the olefins produced include propylene. When the starting olefins include ethylene and n-butene, propylene can be obtained efficiently by a metathesis reaction between ethylene and 2-butene.

In the invention, n-butene may be 2-butene that is required for metathesis reaction with ethylene to produce propylene, or may be 1-butene that is isomerized into 2-butene by the isomerization catalyst in the reactor. Instead of n-butene, a C4 mixture containing n-butene may be used. In the invention, the C4 mixture refers to a mixture of two or more kinds of C4 compounds such as C4 olefins and C4 paraffins, and essentially contains n-butene. Examples of the C4 mixtures include C4 raffinates containing C4 olefins and C4 paraffins. The C4 olefins include n-butene (1-butene, 2-butene) and isobutene. The C4 paraffins include n-butane and isobutane.

The weight of n-butene (the total of 1-butene and 2-butene) is preferably not less than 10%, and more preferably not less than 20% based on the weight of the C4 mixture. The C4 paraffins such as n-butane and isobutane may be contained at any proportions since they do not participate in the metathesis reaction. However, the weight of butane (the total of n-butane and isobutane) is preferably not more than 90%, and more preferably not more than 80% based on the weight of the C4 mixture. Isobutene produces byproducts by a metathesis reaction with 1-butene or 2-butene, but may be contained in the C4 mixture as long as its concentration is not extremely high. The weight of isobutene is preferably not more than 30%, and more preferably not more than 20% based on the weight of the C4 mixture. Preferably, diener such as butadiene and trienes are sufficiently removed from the C4 mixtures by extraction or hydrogenation.

It is ideal for the metathesis reaction that starting olefins do not contain impurities that can poison the catalysts, such as oxygen-containing compounds, sulfur-containing compounds and other heteroatom-containing compounds. However, it is practically very difficult to obtain such starting olefins from the viewpoints of processing and costs.

In the invention, the starting olefin may contain more than 0 ppm by weight to not more than 10 ppm by weight of one or more kinds of heteroatom-containing compounds. The heteroatom-containing compounds may be oxygen-containing compounds and sulfur-containing compounds. The concentration of the heteroatom-containing compounds in the starting olefin may be more than 0 ppm by weight to not more than 10 ppm by weight, preferably more than 0 ppm by weight to not more than 3 ppm by weight, and still more preferably more than 0.1 ppm by weight to not more than 1 ppm by weight. In general, the metathesis catalyst activity is drastically deteriorated when a starting olefin contains impurities such as heteroatom-containing compounds at the above concentration. In the present invention, however, the metathesis reaction is catalyzed by the metathesis catalyst in combination with the isomerization catalyst including calcined hydrotalcite or yttrium oxide. The present invention thereby prevents drastic deterioration of the metathesis catalyst activity by trace impurities such as heteroatom-containing compounds that are contained in the starting olefins.

Examples of the oxygen-containing compounds contained in the starting olefins include, but are not limited to, water, carbon dioxide, alcohols such as methanol, ethanol, n-propanol, isopropanol (IPA), n-butanol, isobutanol and tertiary butanol (TBA), ketones such as acetone and methyl ethyl ketone (MEK), aldehydes such as acetaldehyde, and ethers such as dimethyl ether (DME), diethyl ether (DEE), tertiary amyl methyl ether (TAME), methyl tertiary butyl ether (MTBE) and ethyl tertiary butyl ether (ETBE). In particular, propanol, butanol and acetone are very frequently found in the starting olefins; further, such oxygen-containing compounds have high polarity and are easily adsorbed to the catalysts, greatly affecting the catalytic activity.

Examples of the sulfur-containing compounds contained in the starting olefins include, but are not limited to, carbonyl sulfide (COS), hydrogen sulfide, carbon disulfide, methyl mercaptan, ethyl mercaptan, dimethyl sulfide (DMS), dimethyl disulfide (DMDS), diethyl disulfide (DEDS), methyl ethyl sulfide (MES) and thiophene.

Other heteroatom-containing compounds found in the starting olefins include ammonia, phosphine and arsine, but are not limited thereto.

The heteroatom-containing compounds in the starting olefins may be quantitatively determined by known methods suited for the compounds. For example, DME and MTBE may be quantified by GC-MS (gas chromatography mass spectrometry). The water concentration may be determined by Karl Fischer's method. Acetone, methanol, ethanol, n-propanol, IPA and TBA may be quantitatively determined by passing a prescribed amount of the starting olefin through water to let the water absorb these impurities, then concentrating the water, and analyzing the concentrate by FID-GC. The quantification methods are not limited to those described hereinabove.

Even when these heteroatom-containing compounds are present in the starting olefin, the combination of the metathesis catalyst with the isomerization catalyst including calcined hydrotalcite or yttrium oxide can catalyze the metathesis reaction while preventing the catalysts from degradation, and the metathesis catalyst activity may be maintained for long periods.

The starting olefins may contain, in addition to the olefins subjected to the metathesis reaction, paraffins such as methane, ethane and propane, other olefins that do not participate in the metathesis reaction, hydrogen and nitrogen.

In a preferred embodiment of the invention, a gas containing the starting olefin(s) is supplied to a reactor at a superficial velocity of 0.01 to 2.0 m/sec, and more preferably 0.014 to 1.5 m/sec.

In a representative case where a fixed bed reactor is used and a plug flow is achieved, the superficial velocity in the invention is a linear velocity of the starting olefin gas that passes through the metathesis catalyst and the isomerization catalyst in the reactor. The superficial velocity is represented by Equation (1) below.

[Formula 1]

$$U_{avg}(\text{m/sec})=Fv/[\pi \times (Di/2)^2] \quad (1)$$

$U_{avg}$: superficial velocity (m/sec)
Fv: feed velocity of starting olefin (m$^3$/sec)
Di: inner diameter of reactor (m)

The present inventors have filed Japanese Patent Application No. 2007-118891 directed to a method wherein the by-production of paraffins such as ethane and propane is minimized and the lowering in metathesis catalyst activity is prevented by adding a small amount of hydrogen to the reaction system and controlling the superficial velocity at a high speed as described above. However, the addition of hydrogen inevitably results in trace amounts of paraffins byproduced.

In the invention, the metathesis reaction is catalyzed by the combination of the metathesis catalyst with the isomerization catalyst including calcined hydrotalcite or yttrium oxide, and the processes of the invention prevent catalyst degradation and allow for prolonged metathesis catalyst activity. That is, the present invention does not entail even trace amounts of hydrogen for the prevention of deteriorated activity of the metathesis catalysts, and thus does not cause by-production of paraffins such as ethane and propane due to the addition of hydrogen. By supplying the starting olefin gas at a high superficial velocity as described above, diffusion effects are achieved in the reactor and the catalysts will adsorb less amounts of impurities such as heteroatom-containing compounds present in the starting olefins. As a result, the catalyst degradation is prevented and the metathesis catalyst activity is maintained for long periods, enabling stable and efficient olefin production.

EXAMPLES

Hereinbelow, the present invention will be described in greater detail based on examples without limiting the scope of the invention.

Example 1

Metathesis Catalyst

Ammonium metatungstate was supported on a $SiO_2$ support (shaped product of CARiACT-Q10, manufactured by Fuji Silysia Chemical Ltd.) by impregnation and was calcined in air at 550° C. for 5 hours to give $WO_3/SiO_2$. The $WO_3/SiO_2$ was crushed and sieved to sizes ranging from 150 to 500 μm for use as a metathesis catalyst.
(Isomerization Catalyst)
Powder of calcined hydrotalcite (KW-2000, manufactured by Kyowa Chemical Industry, Ltd.) was compression molded. The compact was crushed and sieved to sizes ranging from 150 to 500 μm for use as an isomerization catalyst.
(Reactor)
A stainless steel tube 8 mm in inner diameter and 420 mm in length was used as a reactor.
1.2 g of the metathesis catalyst ($WO_3/SiO_2$) and 3.38 g of the isomerization catalyst (calcined hydrotalcite (KW-2000, manufactured by Kyowa Chemical Industry, Ltd.)) were packed in the middle of the reactor to form a catalyst layer. Alumina balls were packed in upper and lower portions of the reactor to fix the catalyst layer.
(Propylene Production)
Ethylene and a C4 mixture were supplied to the reactor, and a metathesis reaction was carried out to produce propylene. Details were as described below.

The ethylene used was high-purity ethylene (purity: not less than 99.9%) manufactured by SUMITOMO SEIKA CHEMICALS CO., LTD.), and the C4 mixture was a product manufactured by Mitsui Chemicals, Inc., the applicant of the present invention. FID-GC provided the principal composition of the C4 mixture as follows. The C4 mixture contained trace impurities as shown in Table 1.
Principal Composition of C4 Mixture
  n-Butene (the total of 1-butene and 2-butene): 50 wt %
  Butane (the total of isobutane and n-butane): 36 wt %
  Isobutene: 13 wt %

The temperature in the reactor was increased to 500° C. while a nitrogen gas was passed through the reactor, and the catalysts were reduced by passing a hydrogen gas at 500° C. for 2 hours. The temperature was then lowered to 300° C., which was predetermined as the reaction temperature.

Subsequently, ethylene and the C4 mixture were supplied to the reactor and a metathesis reaction was performed at 300° C. and 3.5 MPaG. The amounts (weights) of ethylene and the C4 mixture supplied per unit time were controlled such that the molar ratio of ethylene to n-butene (the total of 1-butene and 2-butene) (ethylene/n-butene) would be 1.5 and the weight hourly space velocity (WHSV) would be 20 h$^{-1}$. The weight hourly space velocity was a ratio of the amounts (the total weight) of ethylene and n-butene supplied per unit time relative to the amount of the metathesis catalyst ($WO_3/SiO_2$).

At a reaction temperature of 300° C. and a reaction pressure of 3.5 MPaG, the total feeding velocity (Fv) of the starting olefins was 3.3×10$^{-7}$ m$^3$/sec. Based on the reactor's inner diameter (Di) and the total feeding velocity (Fv) of the starting olefins, the superficial velocity in the reactor (U$_{avg}$) was determined to be 0.0065 m/sec from Equation (1) described hereinabove.

The n-butene conversion was balanced at 70.4% and 70.5% after 2 hours and 20 hours after the reaction was initiated, respectively. The conversion stood at a high level of 59.7% even after 40 hours of reaction. In these stages of the reaction, propylene was the main product. The results are set forth in Table 2. The n-butene conversion was calculated from the proportion of n-butene consumed by the reaction.

TABLE 1

Analysis results of trace impurity concentrations

| Trace impurities in C4 mixture | Concentration (ppm by weight) |
|---|---|
| Dimethyl ether (DME) | N.D. |
| Methyl tertiary butyl ether (MTBE) | N.D. |
| Acetone | 0.2 |
| Methanol | N.D. |
| Ethanol | N.D. |
| n-Propanol | N.D. |
| Isopropanol (IPA) | 0.7 |
| n-Butanol | N.D. |
| Tertiary butanol (TBA) | N.D. |

(Note: N.D. indicates no peaks were detected.)

(Analysis of Trace Impurity Concentrations)

The concentrations of trace impurities in the C4 mixture were determined by methods suited for the compounds as follows.

The water concentration was analyzed by Karl Fischer's method, but no peaks were detected.

The concentrations of dimethyl ether (DME) and methyl tertiary butyl ether (MTBE) belonging to ethers were analyzed by GC-MS. The concentrations of acetone belonging to ketones, and methanol, ethanol, n-propanol, isopropanol (IPA), n-butanol and tertiary butanol (TBA) belonging to alcohols were determined by passing 100 g of the C4 mixture through water to let the water absorb these ketone and alcohols, then concentrating the water, and analyzing the concentrate by FID-GC.

The analysis provided peaks assigned to acetone and isopropanol (IPA), with the acetone concentration being 0.2 ppm by weight and the IPA concentration being 0.7 ppm by weight. No peaks assigned to the other impurities were detected.

Example 2

Ammonia water was dropped into an aqueous yttrium nitrate solution to form a precipitate. The precipitate was filtered, washed and calcined at 500° C. for 3 hours to afford yttrium oxide (Y$_2$O$_3$).

A metathesis reaction was carried out and propylene was produced in the same manner as in Example 1, except that 4.8 g of the yttrium oxide (Y$_2$O$_3$) was used as the isomerization catalyst in the catalyst layer.

The n-butene conversion was balanced at 70.3% and 70.4% after 2 hours and 20 hours after the reaction was initiated, respectively. The conversion stood at a high level of 64.3% even after 40 hours of reaction. The results are set forth in Table 2.

Comparative Example 1

A metathesis reaction was carried out and propylene was produced in the same manner as in Example 1, except that 4.8 g of magnesium oxide (MgO, KM-150, manufactured by Kyowa Chemical Industry, Ltd.) was used as the isomerization catalyst in the catalyst layer.

The n-butene conversion was 70.5% after 2 hours after the reaction was initiated, but lowered to 29.4% after 20 hours of reaction. The catalytic activity was completely lost in 40 hours after the reaction was initiated. The results are set forth in Table 2.

Reference Example 1

A metathesis reaction was carried out and propylene was produced in the same manner as in Comparative Example 1, except that the C4 mixture used in Example 1 was purified beforehand with an excess of γ-alumina (NKHD-24, manufactured by Sumitomo Chemical Co., Ltd.). The purified C4 mixture did not give any peaks assigned to acetone or isopropanol (IPA) which were detected in before purification.

The n-butene conversion was balanced at 70.5%, 70.4% and 70.5% after 2 hours, 20 hours and 40 hours after the reaction was initiated, respectively. The results are set forth in Table 2. These results show that the metathesis catalyst activity is drastically enhanced when trace impurities are thoroughly removed from the C4 mixture. In other words, it was indicated that the C4 mixture used in the above examples contained trace impurities.

TABLE 2

|  | Ex. 1 | Ex. 2 | Comp. Ex. 1 | Ref. Ex. 1 |
|---|---|---|---|---|
| Isomerization catalyst | Calcined hydrotalcite | Y$_2$O$_3$ | MgO | MgO |
| Amount of isomerization catalyst (g) | 3.38 | 4.80 | 4.80 | 4.80 |
| Purification of starting olefin | Not performed | Not performed | Not performed | Performed |
| Conversion after 2 hours of reaction (%) | 70.4 | 70.3 | 70.5 | 70.5 |
| Conversion after 20 hours of reaction (%) | 70.5 | 70.4 | 29.4 | 70.4 |
| Conversion after 40 hours of reaction (%) | 59.7 | 64.3 | 0 | 70.5 |

Example 3

Metathesis Catalyst

WO$_3$/SiO$_2$ prepared as described in Example 1 was used as a metathesis catalyst without being crushed and sieved.

(Isomerization Catalyst)

Calcined hydrotalcite, which was produced by Mitsui Chemicals, Inc., was tableted for use as an isomerization catalyst.

(Reactor)

A SUS cylindrical reactor 48.6 mm in outer diameter, 41.2 mm in inner diameter and 2 m in length was used.

180 g of the metathesis catalyst (WO$_3$/SiO$_2$) and 610 g of the isomerization catalyst (calcined hydrotalcite, which was produced by Mitsui Chemicals, Inc.) were packed in the middle of the reactor to form a catalyst layer. Alumina balls were packed in upper and lower portions of the reactor to fix the catalyst layer. The height of the catalyst layer was approximately 1 m.

(Propylene Production)

Ethylene and a C4 mixture were supplied to the reactor, and a metathesis reaction was carried out to produce propylene. Details were as described below.

Under ordinary pressure, the temperature in the reactor was increased to 550° C. and maintained constant for about 10 hours while a nitrogen gas was passed from the top through the bottom of the reactor. At the same temperature, the catalysts were reduced by passing a hydrogen gas and a nitrogen gas for 3 hours. The temperature was then lowered to 300° C., which was predetermined as the reaction temperature.

Subsequently, the inner pressure was held at 2.7 MPaG and a reaction was initiated at 300° C. by supplying a reaction gas.

The reaction gas was composed of ethylene and a C4 mixture. The C4 mixture contained 2-butene (including cis-isomer and trans-isomer), 1-butene, isobutene, isobutane and n-butane. In the C4 mixture, n-butene (the total of 2-butene and 1-butene) accounted for 50 to 60 wt %.

Ethylene and the C4 mixture were supplied to the reactor at 2.1 kg/h and 4.7 kg/h, respectively. At a reaction temperature of 300° C. and a reaction pressure of 2.7 MPaG, the total feeding velocity (Fv) of the starting olefins was $7.6 \times 10^{-5}$ m$^3$/sec, which corresponded to a weight hourly space velocity (WHSV) of 24 h$^{-1}$. The WHSV herein was a ratio of the above supply rates of ethylene and n-butene combined relative to the amount of the metathesis catalyst (WO$_3$/SiO$_2$). Based on the reactor's inner diameter (Di) and the total feeding velocity (Fv) of the starting olefins, the superficial velocity in the reactor ($U_{avg}$) was determined to be 0.055 m/sec from Equation (1) described hereinabove.

The n-butene conversion was 71% after 24 hours of reaction. The reaction was further continued, and the n-butene conversion after 500 hours of reaction was 60%. The results are set forth in Table 3. Gases that were sampled simultaneously at the inlet and the outlet of the reactor were analyzed by FID-GC. The proportion of n-butene consumed by the reaction was calculated from the concentrations of n-butene (the total of 2-butene and 1-butene) in the inlet gas and the outlet gas, thereby obtained the n-butene conversion.

Example 4

Yttrium oxide (Y$_2$O$_3$) prepared as described in Example 2 was extruded. A metathesis reaction was carried out and propylene was produced in the same manner as in Example 3, except that 670 g of the extruded yttrium oxide was used as the isomerization catalyst in the catalyst layer.

The n-butene conversion was 70.3% after 24 hours of reaction. The reaction was further continued, and the n-butene conversion after 500 hours of reaction was 58.7%. The results are set forth in Table 3.

Comparative Example 2

A metathesis reaction was carried out and propylene was produced in the same manner as in Example 3, except that the calcined hydrotalcite isomerization catalyst (manufactured by Mitsui Chemicals, Inc.) was replaced by 790 g of tablets of magnesium oxide (MgO, KM-150, manufactured by Kyowa Chemical Industry, Ltd.).

The n-butene conversion was 70% after 24 hours after the reaction was initiated, but lowered to 40% after 500 hours of reaction. The results are set forth in Table 3.

TABLE 3

|  | Ex. 3 | Ex. 4 | Comp. Ex. 2 |
|---|---|---|---|
| Isomerization catalyst | Calcined hydrotalcite | Y$_2$O$_3$ | MgO |
| Amount of isomerization catalyst (g) | 610 | 670 | 790 |
| Purification of starting olefin | Not performed | Not performed | Not performed |
| Conversion after 20 hours of reaction (%) | 71.0 | 70.3 | 70.0 |
| Conversion after 500 hours of reaction (%) | 60.0 | 58.7 | 40.0 |

[Evaluation of Thermal Stability in Catalyst Regeneration]

Thermal stability of the catalysts in regeneration was evaluated based on the retention (%) of specific surface area of the catalysts. The higher the retention (%) of specific surface area, the higher the thermal stability in catalyst regeneration. The retention (%) of specific surface area was obtained by dividing the specific surface area of the catalyst calcined at 600° C. by the specific surface area of the catalyst calcined at 500° C. The specific surface area of the catalyst calcined at 500° C. or 600° C. was determined as follows. First, the catalyst was calcined in air at 500° C. or 600° C. for 24 hours. Each temperature was reached by raising the temperature at 5° C./min, and air was passed at a rate of 2 liter/min. After the calcination, the temperature was lowered to ambient and the specific surface area was measured by a nitrogen adsorption method.

(Evaluation 1)

Calcined hydrotalcite (KW-2000, manufactured by Kyowa Chemical Industry, Ltd.) was tested to evaluate thermal stability in catalyst regeneration. The results are set forth in Table 4.

(Evaluation 2)

The yttrium oxide (Y$_2$O$_3$) prepared in Example 2 was tested to evaluate thermal stability in catalyst regeneration. The results are set forth in Table 4.

(Evaluation 3)

Magnesium oxide (MgO, KM-150, manufactured by Kyowa Chemical Industry, Ltd.) was tested to evaluate thermal stability in catalyst regeneration. The results are set forth in Table 4. The retention of specific surface area of the magnesium oxide (MgO) was 46%, and the value was very low in contrast to the calcined hydrotalcite.

TABLE 4

|  | Evaluation 1 | Evaluation 2 | Evaluation 3 |
|---|---|---|---|
| Isomerization catalyst | Calcined hydrotalcite | Y$_2$O$_3$ | MgO |
| Specific surface area (m$^2$/g) after calcination at 500° C. for 24 hours | 207 | 58 | 93 |
| Specific surface area (m$^2$/g) after calcination at 600° C. for 24 hours | 193 | 51 | 43 |
| Retention (%) of specific surface area | 93 | 88 | 46 |

The invention claimed is:

1. An olefin production process comprising supplying a starting olefin containing more than 0 ppm by weight to not more than 10 ppm by weight of one or more kinds of heteroatom-containing compounds to a reactor that contains a metathesis catalyst and an isomerization catalyst, the metathesis catalyst including at least one metal element selected from the group consisting of tungsten, molybdenum and rhenium, the isomerization catalyst including calcined hydrotalcite or yttrium oxide, and performing a metathesis reaction of identical or different olefins to produce an olefin having another different structure, wherein a gas containing the starting olefin is supplied to the reactor at a superficial velocity of 0.01 to 2.0 m/sec.

2. The olefin production process according to claim 1, wherein the heteroatom-containing compounds include an oxygen-containing compound.

3. The olefin production process according to claim 2, wherein the oxygen-containing compounds include an alcohol, an ether or a ketone.

4. The olefin production process according to claim 3, wherein the oxygen-containing compounds include propanol, butanol or acetone.

5. The olefin production process according to claim 2, wherein the oxygen-containing compounds include propanol, butanol or acetone.

6. The olefin production process according to claim 1, wherein the concentration of the one or more heteroatom-containing compounds in the starting olefin is more than 0.1 ppm by weight to not more than 1 ppm by weight.

7. The olefin production process according to claim 1, wherein the metathesis catalyst includes tungsten.

8. The olefin production process according to claim 1, further comprising a step of regenerating the metathesis catalyst and the isomerization catalyst at a temperature of 500° C. or above.

9. The olefin production process according to claim 1, wherein the starting olefins include ethylene and n-butene, the metathesis reactions include a metathesis reaction between ethylene and 2-butene, and the olefins produced include propylene.

10. The olefin production process according to claim 1, wherein the metathesis catalyst includes tungsten and is supported on silica, wherein the isomerization catalyst includes calcined hydrotalcite, and wherein the metathesis reaction is performed without adding hydrogen to the reactor.

11. The olefin production process according to claim 10, wherein the concentration of the one or more heteroatom-containing compounds in the starting olefin is more than 0.1 ppm by weight to not more than 1 ppm by weight.

12. The olefin production process according to claim 1, wherein the metathesis catalyst includes tungsten and is supported on silica, wherein the isomerization catalyst includes yttrium oxide, and wherein the metathesis reaction is performed without adding hydrogen to the reactor.

13. The olefin production process according to claim 12, wherein the concentration of the one or more heteroatom-containing compounds in the starting olefin is more than 0.1 ppm by weight to not more than 1 ppm by weight.

* * * * *